United States Patent [19]
Ferres

[11] 3,987,032
[45] Oct. 19, 1976

[54] PENICILLINS
[75] Inventor: Harry Ferres, Horsham, England
[73] Assignee: Beecham Group Limited, Great Britain
[22] Filed: June 3, 1975
[21] Appl. No.: 583,278

[30] Foreign Application Priority Data
June 18, 1974 United Kingdom............... 26887/74

[52] U.S. Cl................................ 260/239.1; 424/271
[51] Int. Cl.²................ C07D 499/68; C07D 499/70
[58] Field of Search.................... 260/239.1; 424/271

[56] References Cited
UNITED STATES PATENTS
3,381,001  4/1968  McGregor........................ 260/239.1
3,654,265  4/1972  Essery et al...................... 260/239.1
3,923,788  12/1975  Fenes et al....................... 260/239.1

FOREIGN PATENTS OR APPLICATIONS
2,181,713  12/1973  France............................. 260/239.1

Primary Examiner—Gerald A. Schwartz

[57] ABSTRACT

The invention provides penicillins of formula (I) their pharmaceutically acceptable salts and esters, a process for their preparation and intermediates from which they may be prepared.

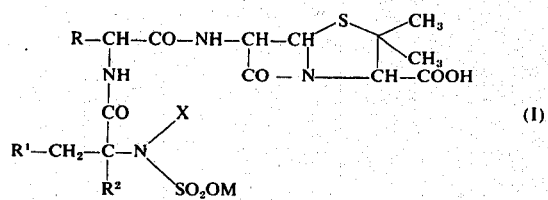

13 Claims, No Drawings

PENICILLINS

This invention relates to new penicillins which have, in general, a broad spectrum of antibacterial activity, being active against many species of Gram-negative and Gram-positive bacteria. They are, therefore, of value as therapeutic agents and prophylactic agents against bacterial infections in animals, including man and poultry. The invention further relates to a method for preparing these compounds, and to their use in therapy.

Although there are now available a number of semi-synthetic penicillins having what is known as broad-spectrum activity, no single penicillin is yet available which has a clinically useful level of antibacterial activity against all the pathogenic organisms encountered in clinical practice. The search thus continues for broad-spectrum penicillins which have advantages, either in improved antibacterial effectiveness or wider spectrum of activity, over the available penicillins.

Accordingly, this invention provides penicillins of formula (I) and pharmaceutically acceptable salts and esters thereof:

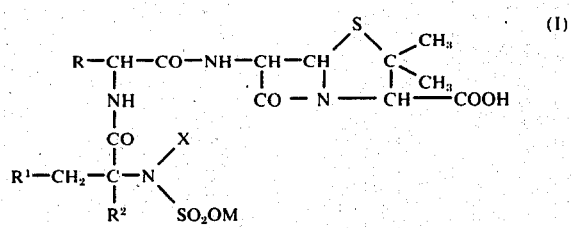

wherein R is phenyl, phenyl substituted by one or more functional groups selected from hydroxy, halogen, nitro, alkoxy containing from 1 to 3 carbon atoms, and amino groups, 2 - or 3 - thienyl, cycloalkyl having from 3 to 7 carbon atoms, cycloalkenyl having from 5 to 7 carbon atoms or alkyl having from 1 to 4 carbon atoms; $R^1$ is hydrogen or an organic radical containing up to 20 carbon atoms; $R^2$ is hydrogen or an alkyl group having from 1 to 3 carbon atoms; X is hydrogen, or a non-functional substituent; and M is hydrogen, or a pharmaceutically acceptable salt forming ion.

The group R may be, for example, phenyl, 4-hydroxyphenyl, 3-chloro-4-hydroxyphenyl, 4-nitrophenyl, 4-chlorophenyl, 4-fluorophenyl, 4-methoxyphenyl, 4-aminophenyl, 2-thienyl, 3-thienyl, cyclopropyl, cyclohexyl, cyclohexa-1,4-dienyl, iso-propyl or methyl.

The group $R^1$ may be, for example, hydrogen; phenyl, phenyl substituted by a group chosen from hydroxy, halogen, nitro, $C_{1-3}$ alkoxy or amino, e.g. 4-hydroxyphenyl, 4-nitrophenyl, 4-chlorophenyl, 4-fluorophenyl, 4-methoxyphenyl, 4-aminophenyl; $C_{1-6}$ alkyl such as methyl, ethyl, n and iso-propyl, n-, sec- and tert-butyl; $C_{1-6}$ alkoxy such as methoxy, ethoxy, n- and iso-propoxy, $C_{1-6}$ alkoxymethyl such as methoxymethyl, ethoxymethyl, n- and iso-propoxymethyl, $C_{1-6}$ alkylthio such as methylthio, ethylthio, n- and iso-propylthio $C_{1-6}$ alkylthiomethyl such as methylthiomethyl, ethylthiomethyl, n- and iso- propylthiomethyl; carbamoyl, carbamoylmethyl, ureido, ureidomethyl, 2-ureidoethyl; acetoxy, and acyloxy such as phenoxy, aralkoxy such as benzyloxy; heterocyclic such as 2-thienyl, 3-thienyl, indol-3-yl, 1H-imadazol-5-yl, $C_{1-6}$ cycloalkenyl such as cyclohexa-1,4-dienyl, 3_3–6 cycloalkyl such as cyclopropyl and cyclohexyl.

The group X is either hydrogen or a non-functional substituent. Examples of typical non-functional substituents include aryl groups, such as phenyl, aralkyl groups such as benzyl and alkaryl groups such as p-tolyl. Preferably R is phenyl, 4-hydroxyphenyl or 3-thienyl. Preferably $R^1$ is phenyl, 4-hydroxyphenyl, indol-3-yl, 1 H-imidazol-5-yl, methylthiomethyl, carbamoyl, 2-ureidoethyl or hydrogen.

Preferably $R^2$ is hydrogen.

Preferably X is hydrogen.

Preferably the carbon atom to which the group R is formula (I) is attached is in the D configuration.

Preferably the carbon atom to which the group $R^2$ in formula (I) is attached is in the D configuration.

Examples of 3-carboxylate salts of compounds (I) include the sodium, potassium, calcium, magnesium or aluminium salts, and ammonium or substituted ammonium salts, for example those with trialkylamines such as triethylamine, procaine, dibenzylamine, triethanolamine, 1-ethylpiperidine, and other amines which have been used to form salts with benzylpenicillins. These same salts may be formed at the side chain sulphonate group, i.e. when M is a salt forming ion, it may be one of the ions listed above.

Examples of suitable pharmaceutically acceptable 3-carboxylate esters of compounds (I) include those which break down readily in the human body to leave the parent acid, e.g. acyloxyalkyl esters such as acetoxymethyl, pivaloyloxymethyl, α-acetoxyethyl, α-acetoxyethyl and α-pivaloyloxyethyl esters and alkoxycarboxylalkyl esters such as methoxy carbonyloxymethyl esters. Other suitable esters of this readily hydrolysable type include lactone, thiolactone and dithiolactone esters (i.e. compounds of formula (I) wherein the 3-carboxy group is esterified to produce a grouping of formula:

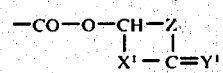

wherein $X^1$ and $Y^1$ are oxygen or sulphur and Z is a divalent hydrocarbon group), especially the phthalide and substituted phthalide esters e.g. 5,6-dimethoxy-phthalide ester.

The compounds of this invention may be prepared by reacting a compound of formula (II) or a salt or ester thereof:

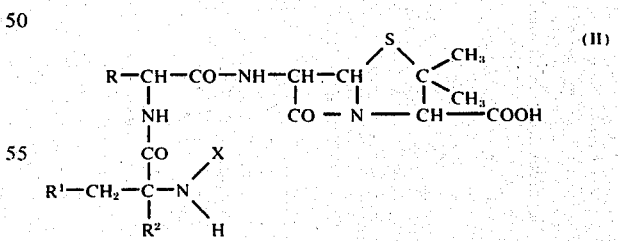

wherein R, $R^1$, $R^2$ and X are as defined in formula (I), with sulphur trioxide, and thereafter if desired reacting the thus formed compound of the formula (I), wherein M is hydrogen, with a base to form a compound of the formula (I) wherein M is a salt forming ion.

The sulphur trioxide reaction with compounds of the formula (II) may be carried out using sulphur trioxide gas in a substantially non-aqueous medium, or by using a complex of sulphur trioxide with an amine such as trimethylamine or pyridine, or with a complex of sulphur trioxide and dioxane.

It is preferred to carry out this process using a sulphur trioxide-trimethylamine complex, and to isolate the product as its salt. In this manner the alkali metal or substituted ammonium salts of the following compounds may be prepared:

D-α-(D-β-phenyl-α-sulphoaminopropionamido)phenylacetamidopenicillanic acid.

D-α(DL-α-sulphoaminobutyramido)-phenylacetamidopenicillanic acid.

D-α(DL-β-phenyl-α-sulphoaminopropionamido)-phenylacetamidopenicillanic acid.

D-α(D-α-sulphoamino-β-4-hydroxyphenylpropionamido)-phenylacetamidopenicillanic acid.

D-α(D-α-sulphoamino-β-4-hydroxyphenylpropionamido)-4-hydroxyphenylacetamidopenicillanic acid.

D-α(D-α-sulphoamino-β-indol-3-ylpropionamido)-phenylacetamidopenicillanic acid.

D-α-(D-α-sulphoamino-β-indol-3-ylpropionamido)-4-hydroxyphenylacetamidopenicillanic acid.

D-α(D-α-sulphoamino-β-1H-imidazol-5-ylpropionamido)-phenylacetamidopenicillanic acid.

D-α(D-α-sulphoamino-β-1H-imidazol-5-ylpropionamido)-4-hydroxyphenylacetamidopenicillanic acid.

D-α(D-α-sulphoamino-Y-methylthiobutyramido)phenylacetamidopencillanic acid.

D-α(D-α-sulphoamino-Y-methylthiobutyramido)-4-hydroxyphenylacetamidopenicillanic acid.

D-α(D-α-sulphoamino-β-carbamoylpropionamido)-4-hydroxyphenylacetamidopenicillanic acid.

D-α(D-α-sulphoamio-α-3-ureidopropylacetamido)-phenylacetamidopenicillanic acid.

D-α(D-α-sulphoamino-α-3-ureidopropylacetamido)-4-hydroxyphenylacetamidopenicillanic acid.

D-α-(D-α-sulphoaminopropionamido)-phenylacetamidopenicillanic acid.

D-α-(D-α-sulphoaminopropionamido)-4-hydroxy-phenylacetamidopenicillanic acid.

D-α(D-α-sulphoamino-β-phenylpropionamido)-4-hydroxyphenylacetamidopenicillanic acid.

If desired, the corresponding free acid may be generated from a thus formed salt by conventional methods. The intermediates of formula (III):

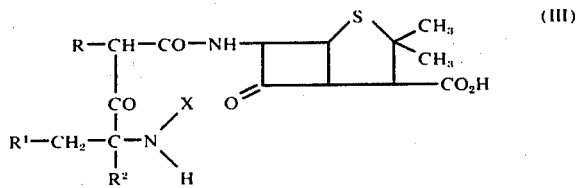

may be prepared by reacting 6-aminopenicillanic acid or a salt, ester or silyl derivative thereof with an N-acylating derivative of an acid of formula (IV)

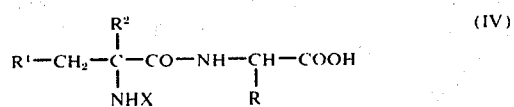

in which any reactive substituents may be blocked, wherein R, $R^1$, $R^2$ and X are as defined in formula (I) and then, if necessary, carrying out one or more of the following steps (i) removing any silyl groups by hydrolysis or alcoholysis, (ii) converting an ester compound to a free acid or salt (iii) converting a salt to a free acid or a free acid to a salt (iv) removing any blocking groups to release the desired functional substituent (v) converting a free acid compound to an ester compound.

By the term "silyl derivative" used in connection with 6-amino-penicillanic acid (6-APA) we mean the product of the reaction between 6-APA and a silylating agent such as a halotrialkylsilane, halodialkylsilane, a halotrialkoxysilane, a dihalodialkoxysilane or a corresponding aryl or aralkyl silane and compounds such as hexamethyldisilazane. In general, halotrialkylsilanes are preferred, especially trimethylchlorosilane.

A reactive N-acylating derivative of the acid (IV) is employed in the above process. The choice of reactive derivative will of course be influenced by the chemical nature of the substituents in the acid. Thus, when the acid contains only acid stable groups, an acid halide is a suitable N-acylating derivative, preferably the acid chloride.

Such reagents would, however, be avoided when an acid labile group was present in the acid (IV). In such cases a suitable N-acylating derivative is a mixed anhydride. For this purpose particularly convenient mixed anhydrides are the alkoxyformic anhydrides.

However, with both the acid chloride and mixed anhydride N-acylating agents we have found that some racemisation may take place. To minimise such unwanted racemisation, we prefer to use an activated ester as the N-acylating agent. Such activated esters, for example the ester formed with 1-hydroxybenzotriazole or, preferably, N-hydroxysuccinimide, may be prepared in situ by the reaction of the acid with the appropriate hydroxy compound in the presence of a carbodiimide, preferably dicyclohexylcarbodiimide.

Other reactive N-acylating derivatives of the acid (II) include the reactive intermediate formed by reaction in situ with a carbodiimide or carbonyldiimidazole, but the literature on the preparation of semi-synthetic penicillins contains examples of other reactive N-acylating derivatives of acids suitable for coupling to 6-APA.

It will be understood, of course, that where a free acid of type (I) or a salt thereof is desired, it may be convenient to carry out the acylation reaction using an ester of 6-APA, and then to remove the ester group. Vice versa, if an ester is required, it may be convenient to carry out the acylation reaction using 6-APA or a salt thereof and thereafter to esterify the free acid.

In the above process, if it is necessary to block any reactive substituents in the acid (IV), conventional chemical blocking groups are known. Thus, if desired, any free amino groups may be blocked by conversion to benzyloxycarbonylamino groups, or the amino group may be blocked as the nitro group which is later converted to the amino group.

The compounds of this invention may also be prepared by a process which comprises reacting a compound of formula (V) or a salt, ester or silyl derivative thereof.

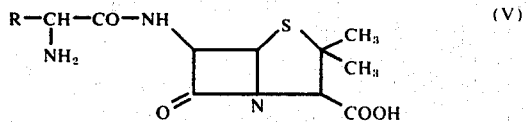

(V)

wherein R is as defined in formula (I) and in which any reactive substituents may be blocked, with an N-acylating derivative of an acid of formula (VI).

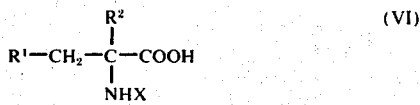

(VI)

wherein $R^1$, $R^2$ and X are as defined in formula (I), and if necessary, carrying out one or more of the following steps (i) removing any silyl groups by hydrolysis or alcoholysis, (ii) converting an ester compound to a free acid or salt thereof (iii) converting a salt to a free acid or a free acid to a salt (iv) removing any blocking groups to release the desired functional substituents (v) converting a free acid compound to an ester compound.

The remarks made earlier with respect to silyl derivatives, N-acylating derivatives, and blocking groups, also apply to this process.

Intermediates of formula (II) where R, $R^1$ and $R^2$ are as defined with reference to formula (I) and X is hydrogen have been disclosed in our co-pending British Application No. 21203/73. The intermediates of formula (II) wherein R, $R^1$, $R^2$ & X are as defined with reference to formula (I) and X is other than hydrogen are novel and therefore provide an additional feature of this invention.

The compounds of this invention are broad spectrum penicillins, i.e. penicillins which not only have activity against Gram-positive bacteria, but also against a number of clinically important Gram-negative organisms. The preferred compounds of this invention are active against such important organisms as Pseudomonas spp. against which the most well known broad-spectrum penicillin (6[(D)α-aminophenylacetamido]-penicillanic acid . . . ampicillin) is normally inactive.

Several of the preferred compounds of this invention show a level of stability to staphylococcal β-lactamase superior to that of many known broad spectrum penicillins. The preferred compounds of this invention are not greatly serum bound, and are not markedly inactivated by serum. They are also of good solubility in aqueous solution.

The penicillins of this invention show the characteristic lack of toxicity of penicillins generally. They may be administered by parenteral injection, or in a few cases by the oral route. The daily dose will depend on the identity of the penicillin and severity of infection. With the preferred compounds of this invention, a suitable average daily dose for an adult would be in the range of 100 mg. and 500 mg. An average single dose for an adult would be from 20 mg. to 500 mg. For administration to animals and human beings, the compounds will generally be presented in combination with one or more pharmaceutically acceptable carriers or excipients of the kind used in formulating penicillin compositions.

The following Examples illustrate the present invention.

EXAMPLE 1

Dipotassium
D-α-[D-β-phenyl-α-sulphoaminopropionamido]-phenylacetamidopenicillanate D-α-[D-α-amino-β-phenylpropionamido]-phenylacetamidopenicillanic acid (5m. mole) in dry dimethylformamide (100 ml.) was treated with triethylamine (1.68 ml; 12m. mole) and stirred till a clear solution resulted.

Sulphur trioxide-trimethylamine complex (0.96 g; 12m. mole) was added portionwise over 5 mins. at room temperature. Stirring was continued for 3 hours. A solution of potassium 2-ethyl hexoate (2.73 g; ca. 15m. mole) in acetone (100 ml.) was added causing a white solid to crystallise. On dilution further with acetone (200 ml.) the solid was filtered, washed with acetone and then stirred for 20 mins. with dry ether (500 ml.) to ensure complete removal of dimethylformamide. The solid was filtered, washed with dry ether and quickly transferred to a vacuum desiccator over phosphorus pentoxide to dry.

Yield: 74.5%

$\nu$max (Nujol): 3300, 3120, 1780, 1658, 1612, 1508, 1205 and 1035 cm$^{-1}$ δ[$D_2O$]: 1.45 (6H.d. gem-dimethyls); 2.7 – 3.1 (2H m. PhC$\underline{H}_2$CH<); 4.17 (1H.s. C-3 proton); 4.0 – 4.4 (1H.m. PhCH$_2$C$\underline{H}$); 5.2 – 5.5 (3H.m. β-lactams PhC$\underline{H}$<); 7.1. – 7.5 (10H. 2s(broad) aromatics)

Hydroxylamine Assay 89%

Biochromatography: Rf = 0.15

EXAMPLE 2

Dipotassium
D-α-[DL-α-sulphoaminobutyramido]-phenylacetamidopenicillanate

The title compound was prepared from D-α-(DL-α-aminobutyramido]-phenylacetamidopenicillanic acid by the method of Example 1. Yield: 98%

$\nu$max (KBr): 3430, 1765, 1660, 1610, 1540, 1210, 1048, 700 and 622 cm$^{-1}$

NH$_2$OH assay: 77%

Biochromatography: 1 zone at $R_f$ = 0.05

EXAMPLE 3

Triethylammonium
D-α-(DL-β-phenyl-α-sulphoaminopropionamido]-phenylacetamidopenicillanate The title compound was prepared from D-α-[D,L-α-amino-β-phenylpropionamido]-phenylacetamidopenicillanic acid by the method of Example 1, except that the reaction was carried out in dry methylene dichloride, 6 m, moles of sulphur trioxide-trimethylamine complex was used and the product (the title compound) crystallised out as the triethylammonium salt.

Yield: 29.5%

$\nu$max (KBr): 3430 (br), 3290, 1770, 1637, 1540, 1228, 1040, 750 and 701 cm$^{-1}$.

δ[(CD$_3$)$_2$CO]: 1.15 (9H.t. J = 7Hz HN$^+$ (CH$_2$C$\underline{H}_3$)$_3$); 1.45 (3H.s. gem methyl); 1.60 (3H.s. gem-methyl);~3(2H.m. PhC$\underline{H}_2$ CH<); 3.05 (6H.q. J = 7Hz HN$^+$ (C$\underline{H}_2$CH$_3$)~4(1H.m. PhCH$_2$C$\underline{H}$<); 4.12 (1H.s. C-3 proton); 5.4 (2H.m. β-lactams); 5.73 (1H.d. J =

8Hz PhC<u>H</u><); >6.3 (~6H broad signal*); 7.31 (10H.m. P<u>h</u>CH<, P<u>h</u>CH₂CH 8.58 (1H.d. J = 8Hz PnCHN<u>H</u>CO-‡); 9.24 (1H.d. - CON<u>H</u>-*).

* Removable with D₂O ‡only slowly removable with D₂O

Hydroxylamine Assay: 60.8%
Biochromatography: $R_f = 0.29$

EXAMPLE 4

Disodium D-α-[D-α-sulphoamino-3-(3'-indolylpropionamido)]-phenylacetamido penicillanate D-α-[D-α-amino-3-(3'-indolylpropionamido)]-phenylacetamido penicillanic acid (2.67g; 0.005M) was treated with triethylamine (1.68 ml.) in a mixture of methylene dichloride (100 ml.) and dimethylformamide (20 ml.) was stirred at ambient temperatures until a clear solution was obtained.

Sulphur trioxide - trimethylamine complex (1.68g; 0.012M) was added in 2 portions over 5 mins. and the reaction stirred at room temperature for 3 hours. A solution of sodium 2-ethylhexoate (2.5g) in dry acetone (100 ml.) was added, which precipitated a white gelatinous solid. A further portion of acetone (100 ml.) was added and the solution stirred for 10 mins. and then filtered. The sticky solid was quickly transferred into ether (500 ml.) and stirred for 20 mins. The solid was filtered, washed well with dry ether to give a free-flowing amorphous, white solid in 80% yield. The product was stored in a vacuum desiccator over phosphorus pentoxide overnight.

Hydroxylamine Assay: 70.6%
Biochromatography: $R_f = 0.20$
($R_f$ of starting aminopenicillin = 0.49)
νmax (KBr) bands inter alia at: 3400 (broad), 1785, 1690, 1600, 1615, 1510, 1400, 1220 and 1050cm⁻¹
δ[D₂O]: 1.45 (6H,m, gem dimethyls); 3.05 - 3.40 (2H,m, C<u>H</u>₂-indolyl); 4.12 (1H,s, C-3 proton); 5.0 - 5.6 (3H, β-lactams + α-proton); 7.0 - 7.8 (11H,m, aromatic protons).

EXAMPLE 5

Disodium D-α[D-α-Sulphoamino-γ-methylthiobutyramido]-phenylacetamido penicillanate The title compound was prepared on a 2.5 mM scale from D-α-[D-α-amino-γ-methylthiobutyramido]-phenylacetamido penicillanic acid in 90% yield by the method described for Example 1.

The product was a white amorphous solid.
Biochromatography: $R_f = 0.12$
νmax (KBr) strong bands inter alia at: 3400 (broad): 1785, 1686, 1655, 1610, 1510, 1220 and 1055cm⁻¹
δ[D₂O]: 1.45 (3H,s, gem methyl); 1.50 (3H,s, gem methyl); 1.8 - 2.2 (2H,m, SCH₂C<u>H</u>₂CH); 2.1 (3H,s, C<u>H</u>₃S-); 2.5-2.85 (2H,m,-SC<u>H</u>₂CH₂-); 4.22 (1H,s, C-3 proton); 5.51 (2H,m, β-lactam protons); 7.44 (5H,s, aromatics).

What I claim is:

1. A compound of formula (I), or a pharmaceutically acceptable salt or a conventional penicillin ester thereof:

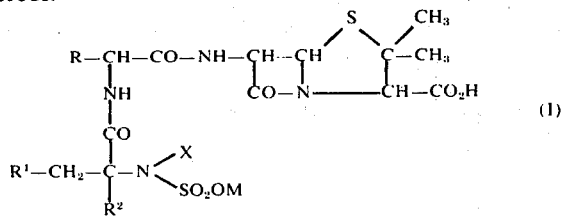

(I)

wherein R is phenyl, or phenyl substituted by one or more groups chosen from hydroxy, halogen, nitro, $C_{1-3}$ alkoxy, or amino; 2- or 3- thienyl, $C_3$ and $C_7$ cycloalkyl, $C_5$ to $C_7$ cycloalkenyl or $C_1$ to $C_4$ alkyl; $R^1$ is hydrogen or an organic radical containing up to 20 carbon atoms selected from the group consisting of phenyl, phenyl substituted by a hydroxy, halogen, or nitro group, $C_{1-6}$ alkyl, $C_{1-6}$ alkoxy, amino, $C_1$–$C_6$ alkoxymethyl, $C_{1-6}$ alkylthio, $C_{1-6}$ alkylthiomethyl, carbamoyl, carbamoylmethyl, ureido, ureidomethyl, ureidoethyl, acetoxy, phenoxy, aralkoxy, 2-thienyl, 3-thienyl, indol-3-yl, 1H-imidazol-5-yl, cyclohexa-1,4-dienyl, and $C_{3-6}$ cycloalkyl; $R^2$ is a $C_1$ to $C_3$ alkyl group, X is hydrogen or a non-functional substituent selected from the group consisting of aryl and aralkyl groups; M is hydrogen or a pharmaceutically acceptable salt forming ion.

2. A compound as claimed in claim 1 wherein $R^1$ is hydrogen, phenyl or phenyl substituted by a group chosen from hydroxy, halogen, nitro, $C_1$ to $C_3$ alkoxy or amino; $C_1$ to $C_6$ alkyl, $C_3$ – $C_6$ cycloalkyl, cyclohexa-1,4-dienyl, $C_1$ to $C_6$ alkylthio methyl, carbamoyl, carbamoylmethyl, ureido, ureidomethyl, 2-ureidoethyl, acetoxy, phenoxy, benzyloxy, 2- or 3-thienyl, indol-3-yl or 1H-imidazol-5-yl.

3. A compound as claimed in claim 1 wherein R is phenyl, 4-hydroxyphenyl, or 3-thienyl.

4. A compound as claimed in claim 1 wherein $R^1$ is phenyl, 4- hydroxyphenyl, indol-3-yl, or 1,4-imidazol-5-yl.

5. A compound as claimed in claim 1 wherein $R^2$ is hydrogen.

6. A compound as claimed in claim 1 wherein X is hydrogen.

7. A compound as claimed in claim 1 wherein the carbon to which the group R is formula (I) is attached is in the D-configuration.

8. A compound as claimed in claim 1 wherein the carbon to which the group $R^2$ in formula (I) is attached is in the D-configuration.

9. A compound selected from the group:

D-α-(D-β-phenyl-α-sulphoaminopropionamido) phenylacetamidopenicillanic acid;
D-α(DL-α-sulphoaminobutyramido)-phenylacetamidopenicillanic acid;
D-α(DL-β-phenyl-α-sulphoaminopropionamido) phenylacetamidopenicillanic acid;
D-α(D-α-sulphoamino-β-4-hydroxyphenylpropionamido) phenylacetamidopenicillanic acid;
D-α(D-α-sulphoamino-β-4-hydroxyphenylpropionamido)-4-hydroxyphenylacetamidopenicillanic acid;
D-α(D-α-sulphoamino-β-indol-3-ylpropionamido)-phenylacetamidopenicillanic acid;
D-α-(D-α-sulphoamino-β-indol-3-ylpropionamido)-4-hydroxyphenylacetamidopenicillanic acid;
D-α(D-α-sulphoamino-β-1H-imidazol-5-ylpropionamido)phenylacetamidopenicillanic acid;
D-α(D-α-sulphoamino-β-1H-imidazol-5-ylpropionamido)-4-hydroxyphenylacetamidopenicillanic acid;

D-α(D-α-sulphoamino-γ-methylthiobutyramido)-phenylacetamidopenicillanic acid;
D-α(D-α-sulphoamino-γ-methylthiobutyramido)-4-hydroxyphenylacetamidopenicillanic acid;
D-α(D-α-sulphoamino-β-carbamoylpropionamido)-4-hydroxyphenylacetamidopenicillanic acid;
D-α(D-α-sulphoamino-α-3-ureidopropylacetamido)-phenylacetamidopenicillanic acid;
D-α(D-α-sulphoamino-α-3-ureidopropylacetamido)-4-hydroxyphenylacetamidopenicillanic acid;
D-α-(D-α-sulphoaminopropionamido)-phenylacetamidopenicillanic acid;
D-α-(D-α-sulphoaminopropionamido)-4-hydroxyphenylacetamidopenicillanic acid; and
D-α-(D-α-sulphoamino-β-phenyl-propionamido)-4-hydroxyphenylacetamidopenicillanic acid.

10. A compound as claimed in claim 1 wherein the ester is phthalidyl, 5,6-dimethyl-phthalidyl, pivaloyloxymethyl or acetoxymethyl 3-carboxylate ester.

11. A compound as claimed in claim 1 which is the sodium, potassium, magnesium, calcium or aluminium sulphonate or carboxylate salt.

12. A compound as claimed in claim 1 which is the triethylamine, procaine, dibenzylamine, triethanolamine, or 1-ethylpiperidine sulphonate or carboxylate salt.

13. A pharmaceutical composition having anti-bacterial activity comprising a compound as claimed in claim 1 together with one or more pharmaceutically acceptable carriers.

* * * * *

UNITED STATES PATENT AND TRADEMARK OFFICE
CERTIFICATE OF CORRECTION

PATENT NO. : 3,987,032
DATED : October 19, 1976
INVENTOR(S) : Harry Ferres

It is certified that error appears in the above–identified patent and that said Letters Patent are hereby corrected as shown below:

Column 1, line 67: "33-6" should read --$C_{3-6}$--.

Column 8, line 3: "$C_3$ and $C_7$" should read --$C_3$ to $C_7$--.

Claim 7, line 2: "R is" should read --R in--.

Signed and Sealed this

First Day of February 1977

[SEAL]

Attest:

RUTH C. MASON
Attesting Officer

C. MARSHALL DANN
Commissioner of Patents and Trademarks